US010722186B2

(12) United States Patent
Nishi (10) Patent No.: US 10,722,186 B2
(45) Date of Patent: Jul. 28, 2020

(54) MAMMOGRAPHY APPARATUS

(71) Applicant: FUJIFILM CORPORATION, Minato-ku, Tokyo (JP)

(72) Inventor: Yoshihiro Nishi, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 173 days.

(21) Appl. No.: 15/922,945

(22) Filed: Mar. 16, 2018

(65) Prior Publication Data
US 2018/0279971 A1    Oct. 4, 2018

(30) Foreign Application Priority Data
Mar. 30, 2017 (JP) ................. 2017-068570

(51) Int. Cl.
*A61B 6/02*    (2006.01)
*A61B 6/00*    (2006.01)
(Continued)

(52) U.S. Cl.
CPC ............ *A61B 6/027* (2013.01); *A61B 6/025* (2013.01); *A61B 6/0414* (2013.01); *A61B 6/107* (2013.01);
(Continued)

(58) Field of Classification Search
CPC .......... A61B 6/027; A61B 6/04; A61B 6/025; A61B 6/0414; A61B 6/107; A61B 6/44;
(Continued)

(56) References Cited

U.S. PATENT DOCUMENTS 3,901,550 A * 8/1975 Hamy ................... B60R 21/02
                                              297/486
7,197,109 B2 * 3/2007 Rotondo ................. A61B 6/14
                                              378/196
(Continued)

FOREIGN PATENT DOCUMENTS

DE    102006007833 A1    8/2006
DE    102008062033 A1    6/2010
(Continued)

OTHER PUBLICATIONS

Extended European Search Report dated Aug. 1, 2018, issued in corresponding EP Patent Application No. 18160631.0.
(Continued)

*Primary Examiner* — Blake C Riddick
(74) *Attorney, Agent, or Firm* — SOLARIS Intellectual Property Group, PLLC (57) ABSTRACT

A mammography apparatus includes: a radiation source that emits radiation to mammae of a test subject; a support part that supports the radiation source to be rotatable around an axis and moves the radiation source to a plurality of imaging positions where incidence angles of the radiation to the mammae are different from each other; a face guard that protects the test subject from the radiation emitted from the radiation source; and at least one pair of arms that is rotatably connected to the face guard at one end thereof, is rotatably connected to a holding part that maintains a stationary state with respect to the rotation of the radiation source at the other end thereof, includes a bending part between the one end and the other end, and is rotatable around a rotation axis that connects the one end and the other end.

12 Claims, 8 Drawing Sheets

(51) Int. Cl.
*A61B 6/04* (2006.01)
*A61B 6/10* (2006.01)
(52) U.S. Cl.
CPC .......... *A61B 6/4429* (2013.01); *A61B 6/4476* (2013.01); *A61B 6/502* (2013.01)
(58) Field of Classification Search
CPC ... A61B 6/4429; A61B 6/4435; A61B 6/4476; A61B 6/502
See application file for complete search history.

(56) References Cited

U.S. PATENT DOCUMENTS

| | | | |
|---|---|---|---|
| 2002/0150214 A1* | 10/2002 | Spahn | A61B 6/4233 378/189 |
| 2004/0161075 A1* | 8/2004 | Amitani | A61B 6/0457 378/37 |
| 2005/0129172 A1* | 6/2005 | Mertelmeier | A61B 6/502 378/37 |
| 2006/0126794 A1* | 6/2006 | Hermann | A61B 6/0414 378/180 |
| 2009/0129556 A1* | 5/2009 | Ahn | A61B 6/04 378/208 |
| 2009/0220055 A1* | 9/2009 | Nakata | A61B 6/0414 378/208 |
| 2009/0323892 A1 | 12/2009 | Hitzke et al. | |
| 2010/0014634 A1* | 1/2010 | Ullberg | A61B 6/0414 378/37 |
| 2010/0183119 A1 | 7/2010 | Ludwig et al. | |
| 2011/0002519 A1* | 1/2011 | Tomisaki | A61B 6/12 382/131 |
| 2011/0075791 A1* | 3/2011 | Nakayama | A61B 6/022 378/4 |
| 2012/0051502 A1* | 3/2012 | Ohta | A61B 6/00 378/37 |
| 2013/0331682 A1* | 12/2013 | Ohta | A61B 6/107 600/407 |
| 2014/0027650 A1* | 1/2014 | Agano | A61B 6/022 250/393 |
| 2014/0213895 A1* | 7/2014 | Kuwabara | A61B 6/022 600/424 |
| 2015/0025377 A1 | 1/2015 | Nishi et al. | |
| 2015/0139518 A1* | 5/2015 | Oohashi | A61B 6/461 382/131 |
| 2018/0110484 A1* | 4/2018 | Kobayashi | A61B 6/0414 |

FOREIGN PATENT DOCUMENTS

| | | |
|---|---|---|
| EP | 3381372 A1 | 10/2018 |
| JP | 2007-252552 A | 10/2007 |
| JP | 2012-501750 A | 1/2012 |
| JP | 2015-19977 A | 2/2015 |
| JP | 2015-019977 A | 2/2015 |
| JP | 2017-012350 A | 1/2017 |

OTHER PUBLICATIONS

Office Action dated Mar. 13, 2019, issued by the EPO in corresponding EP Patent Application No. EP18160631.0.

* cited by examiner

MAMMOGRAPHY APPARATUS

CROSS-REFERENCE TO RELATED APPLICATION

This application claims priority under 35 USC 119 from Japanese Patent Application No. 2017-068570 filed on Mar. 30, 2017, the disclosure of which is incorporated by reference herein in its entirety.

BACKGROUND OF THE INVENTION

1. Field of the Invention

The present invention relates to a mammography apparatus.

2. Description of the Related Art

A mammography apparatus that emits radiation toward mammae of a test subject from a radiation source and detects the radiation that passes through the mammae using a radiation detector to capture a radiation image is known. Generally, in the mammography apparatus, a protection member such as a so-called face guard is provided to protect the test subject from the radiation emitted from the radiation source.

For example, JP2015-19977A discloses a mammography apparatus that includes a radiation protecting unit capable of enlarging or reducing a protection range.

Further, for example, JP2012-501750A discloses a mammography apparatus that includes a face shield that is movably supported by an extension arm.

SUMMARY OF THE INVENTION

However, in the techniques disclosed in JP2015-19977A and JP2012-501750A, for example, in the case of so-called tomosynthesis imaging in which imaging is performed while moving a radiation source, the size of a protection member increases according to a movement range of the radiation source, or the protection member is moved, and thus, the entire size of the apparatus may increase.

The present disclosure has been made in consideration of the above-mentioned problems, and an object of the invention is to provide a mammography apparatus that performs imaging while moving a radiation source, and capable of reducing an increase in the size of the apparatus in a case where a protection member that protects a test subject is provided.

In order to achieve the above-described object, according to an aspect of the present disclosure, there is provided a mammography apparatus comprising: a radiation source that emits radiation to mammae of a test subject; a support part that supports the radiation source to be rotatable around a first rotation axis and moves the radiation source to a plurality of imaging positions where incidence angles of the radiation to the mammae are different from each other; a protection member that protects the test subject from the radiation emitted from the radiation source; and at least one pair of arms that is rotatably connected to the protection member at one end thereof, is rotatably connected to a stationary part that maintains a stationary state with respect to the rotation of the radiation source at the other end thereof, includes a bending part between the one end and the other end, and is rotatable around a second rotation axis that connects the one end and the other end.

In the mammography apparatus according to this aspect of the present disclosure, the pair of arms may be rotated outside an irradiation field of the radiation.

In the mammography apparatus according to this aspect of the present disclosure, the pair of arms may include an arm that is rotated in a case where the support part is rotated in a first direction from an initial state, and an arm that is rotated in a case where the support part is rotated in a second direction from the initial state.

In the mammography apparatus according to this aspect of the present disclosure, the arms may be rotated in a direction where the support part is rotated.

In the mammography apparatus according to this aspect of the present disclosure, the arms may be rotated by being pressed by the support part in accordance with the rotation of the support part.

In the mammography apparatus according to this aspect of the present disclosure, the stationary part may include detachable connection parts to which the arms are detachably connected.

In the mammography apparatus according to this aspect of the present disclosure, each bending part of the pair of arms may protrude upward in a case where the support part is not rotated.

In the mammography apparatus according to this aspect of the present disclosure, a force may be applied to each of the pair of arms in a direction where the support part returns to an initial state from a rotated state.

In the mammography apparatus according to this aspect of the present disclosure, in a case where a state where the support part is not rotated is referred to as an initial state, each of the pair of arms may be in contact with the support part in the initial state.

In the mammography apparatus according to this aspect of the present disclosure, the stationary part may hold an imaging stand that includes an imaging surface that is in contact with the mammae of the test subject, and a pressing plate that presses the mammae.

According to the present disclosure, in a mammography apparatus that performs imaging while moving a radiation source, in a case where a protection member that protects a test subject is provided, it is possible to reduce an increase in the size of the apparatus.

DESCRIPTION OF THE PREFERRED EMBODIMENTS

Hereinafter, embodiments of the invention will be described in detail with reference to the accompanying drawings. The embodiments do not limit the invention.

First, an example of an entire configuration of a mammography apparatus according to this embodiment will be described with reference to FIG. 1.

A mammography apparatus 10 according to this embodiment is an apparatus that individually emits radiation (for example, X-rays) to right and left mammae of a test subject to individually capture radiation images of the right and left mammae. The mammography apparatus 10 may be an apparatus that images mammae of a test subject in a state where the test subject is standing (standing position state), or in a state where the test subject sits on a chair (including a wheelchair) (sitting position state). That is, it is sufficient as long as the mammography apparatus 10 is an apparatus capable of individually imaging at least the right and left mammae of the test subject.

Further, the mammography apparatus 10 according to this embodiment has a function of performing so-called tomosynthesis imaging (of which details will be described later). In this embodiment, imaging other than the tomosynthesis imaging is referred to as "normal imaging".

In addition, in the following description, it is assumed that a side (breast wall side) close to a test subject in a case where the test subject faces the mammography apparatus 10 in capturing a radiation image is an apparatus front side of the mammography apparatus 10 and a side distant from the test subject in a case where the test subject faces the mammography apparatus 10 is an apparatus rear side of the mammography apparatus 10. Further, in the description, it is assumed that a lateral direction of the test subject in a case where the test subject faces the mammography apparatus 10 is an apparatus lateral direction of the mammography apparatus 10. In addition, in the description, it is assumed that a direction in which the side of the head of the test subject is an upper side and the side of the feet is a lower side in a case where the test subject faces the mammography apparatus 10 is a vertical direction.

Figure 1:
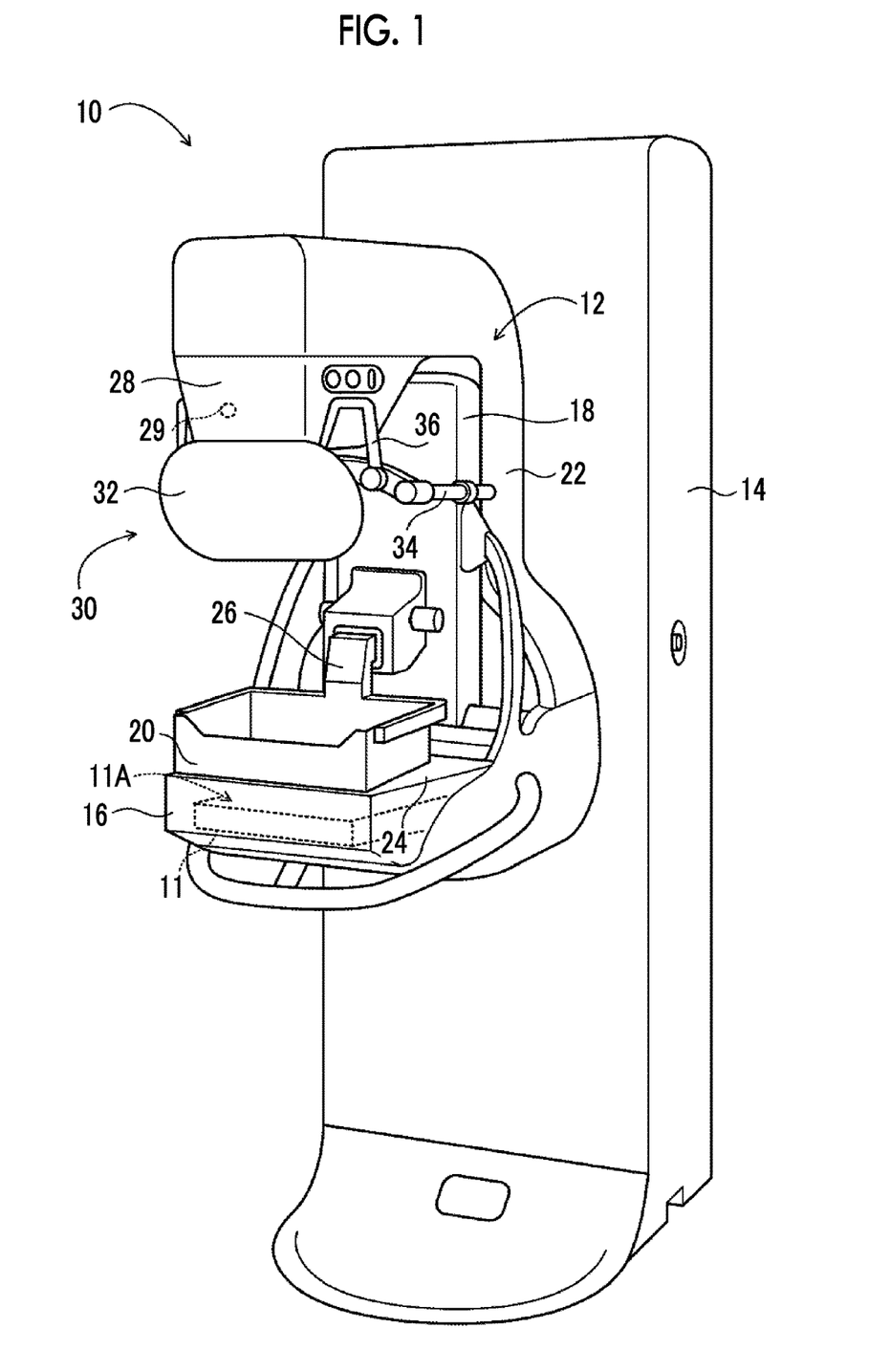
FIG. 1 is a perspective view showing an example of an entire configuration of a mammography apparatus according to an embodiment, when seen from a breast wall side of a test subject.

As shown in FIG. 1, the mammography apparatus 10 includes an imaging part 12 of an approximately C-shape in a side view, provided on a front side of the apparatus, and a base stand part 14 that supports the imaging part 12 from a rear side of the apparatus.

The imaging part 12 includes an imaging stand 16 having a planar imaging surface 24 that is in contact with mammae of a test subject in a standing position state, a pressing plate 20 for pressing the mammae in a state where the mammae is interposed between the imaging surface 24 of the imaging stand 16 and the pressing plate 20, and a holding part 18 that supports the imaging stand 16 and the pressing plate 20. A member that transmits radiation is used for the pressing plate 20.

Further, the imaging part 12 includes a radiation emission part 28 in which a radiation source 29 including a bulb (in this embodiment, for example, tungsten) that emits radiation to the mammae is provided, and a support part 22 that is spaced from the holding part 18 and supports the radiation source 29.

In addition, an axis 23 (see FIG. 8) is provided in the imaging part 12, so that the imaging part 12 is able to rotate with respect to the base stand part 14 (in the lateral direction of the test subject) using the axis 23 as a rotation axis. The axis 23 is fixed with respect to the support part 22, and the axis 23 and the support part 22 are integrally rotated. The axis 23 in this embodiment is an example of a first rotation axis according to the present disclosure.

Gears are respectively provided in the axis 23 and the holding part 18 provided in the imaging part 12, and an engagement state and a non-engagement state of the gears are switched, so that a state where the holding part 18 and the axis 23 are connected to each other to integrally rotate and a state where the axis 23 is spaced from the holding part 18 to idly rotate can be switched. Switching between transmission of power of the axis 23 and non-transmission thereof is not performed only by the above-mentioned gears, but may also be performed by a variety of machine elements.

The holding part 18 holds the imaging stand 16 at a position where the imaging surface 24 is spaced from the radiation source 29 by a predetermined interval. Further, the holding part 18 also holds the pressing plate 20 through a support arm 26, in which the holding part 18 slides the support arm 26, so that the pressing plate 20 moves and an interval between the pressing plate 20 and the imaging surface 24 is thus changed. The holding part 18 in this embodiment corresponds to an example of a stationary part according to the present disclosure.

The imaging surface 24 with which the mammae of the test subject are in contact is formed of carbon from a viewpoint of radiability or strength, for example. Inside the imaging stand 16, a radiation detector 11 that detects radiation that passes through the mammae and the imaging surface 24 is disposed. A radiation image is generated on the basis of the radiation detected by the radiation detector 11. The type of the radiation detector 11 according to this embodiment is not particularly limited, and for example, may be a radiation detector of an indirect conversion type that converts radiation into light and converts the converted light into electric charges, or may be a radiation detector of a direct conversion type that directly converts radiation into electric charges. In this embodiment, image data indicating a radiation image output from the radiation detector 11 of the mammography apparatus 10 is transmitted to an external console (not shown) that controls the mammography apparatus 10.

Figure 2:
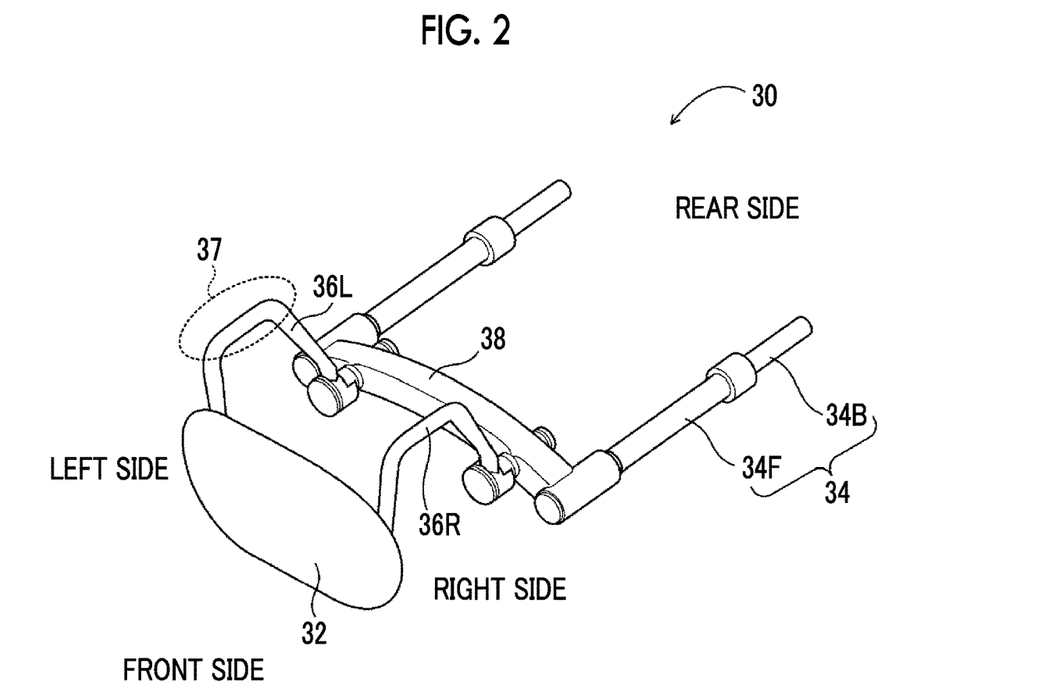
FIG. 2 is a perspective view showing an example of a configuration of a protection part in the mammography apparatus according to the embodiment, when seen from a front side.

In the mammography apparatus 10 of this embodiment, a protection part 30 for protecting a test subject from radiation is detachably provided in the holding part 18. As shown in FIG. 2, or the like, the protection part 30 of this embodiment includes a face guard 32, a pair of attachment parts 34, a pair of arms 36 (36R and 36L) having a bending part 37, and a connection part 38. The protection of the test subject from radiation means preventing the test subject from being directly irradiated with radiation by preventing the test subject (particularly, a head portion of the test subject) from moving toward a radiation source side.

The face guard 32 has a function of a protection member that protects a test subject. In a case where imaging for a radiation image is performed, more specifically, in a case where radiation is emitted from the radiation source 29 to mammae of the test subject, the face of the test subject is pressed against the face guard 32. The face guard 32 is formed of, for example, resin, the same material as that of the pressing plate 20, or the like.

The face guard 32 of this embodiment has a so-called elliptical shape that is a combination of a circle and a rectangle in which protruding curves are drawn on the left and right of the test subject (in the apparatus lateral direction), for example. In the following description, it is assumed that a direction in the face guard 32 corresponding to the apparatus lateral direction in a state where the protection part 30 is attached to the holding part 18 is a lateral direction of the face guard 32.

One end of the arm 36L is rotatably attached to a left portion of a surface opposite to a surface of the face guard 32 on which the face of the test subject is pressed, and one end of the arm 36R is rotatably attached to a right portion thereof, respectively. In this embodiment, when generally referring to the arm 36L and the arm 36R without distinction, the arm 36L and the arm 36R are referred to as "arms 36" without the letters (L, R) for distinction.

Figure 3:
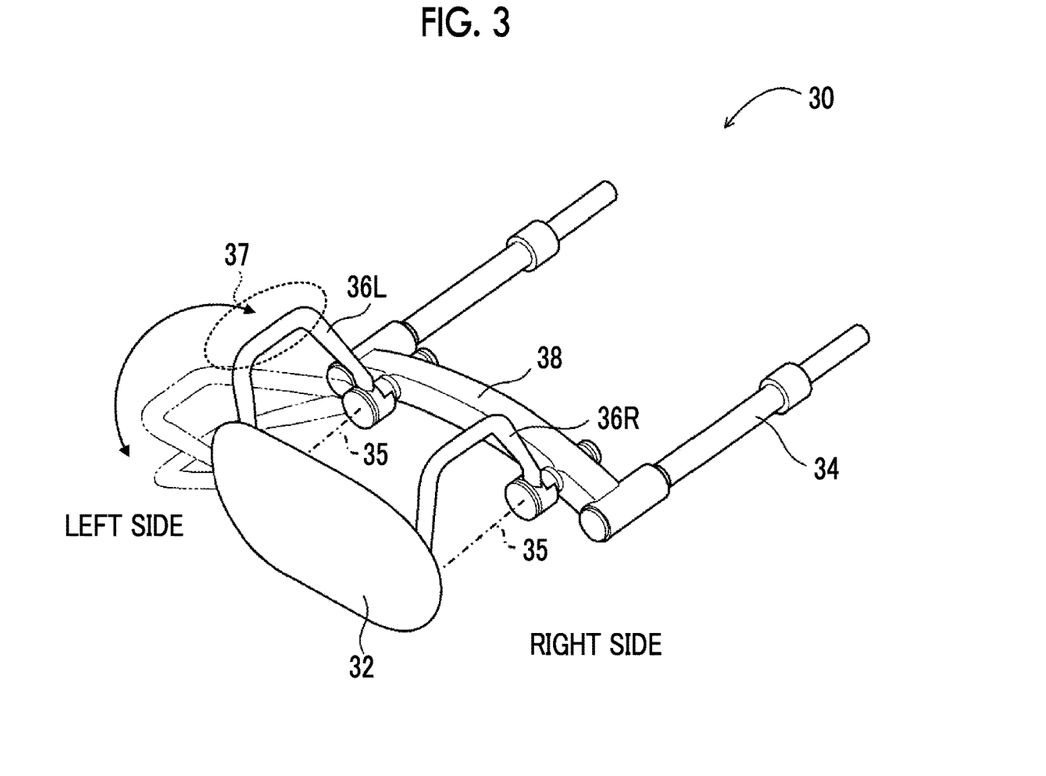
FIG. 3 is a perspective view for illustrating rotation of an arm of the protection part in the mammography apparatus according to the embodiment, when seen from a front side.
Figure 4:
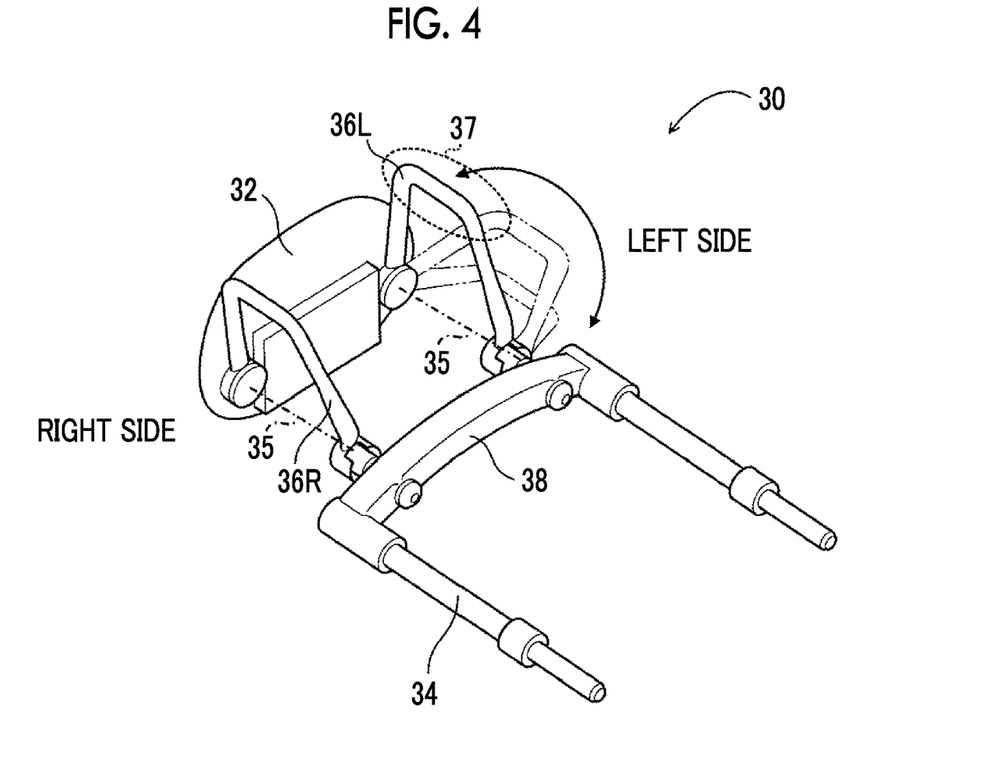
FIG. 4 is a perspective view showing the example of the configuration of the protection part in the mammography apparatus according to the embodiment, when seen from a rear side.

The other end of each arm 36 is rotatably attached to the connection part 38. The arm 36 is configured to be rotatable around a rotation axis 35 (see FIGS. 3 and 4) that connects the one end and the other end of the arm 36. The rotation axis 35 (see FIGS. 3 and 4) of the arm 36 is approximately parallel to the axis 23 that is a rotation axis of the support part 22. The rotation axis 35 of this embodiment corresponds to an example of a second rotation axis of the present disclosure.

For example, in a normal state where the support part 22 is not rotated, as shown in FIG. 2, or the like, the arm 36 is disposed in a state where the bending part 37 protrudes upward. Hereinafter, this state is referred to as an "initial state" of the arm 36. The arm 36 is rotated around the rotation axis 35 of the arm 36 in a direction where the support part 22 is rotated from the initial state in accordance with the rotation of the support part 22 (see an arrow in FIGS. 3 and 4).

The arm 36 and the connection part 38 are formed of, for example, aluminum, or the like. A portion of the arm 36 (of which details will be described later) that is in contact with the support part 22 may have a configuration in which a surface of aluminum is covered with an elastic member, or may be formed using an elastic member instead of aluminum.

Further, a force (so-called biasing force) is applied to the arm 36 in a direction where the arm 36 returns to the initial state from the rotated state by a spring (not shown) or the like.

On the other hand, the pair of attachment parts 34 is respectively provided in left and right ends of the connection part 38, and has a function for attaching the face guard 32 to the holding part 18. Each of the attachment part 34 includes an insertion part 34B and a support part 34F. The insertion part 34B of the attachment part 34 is formed of, for example, stainless steel, or the like. Further, the support part 34F of the attachment part 34 is formed of, for example, an iron pipe, or the like.

Figure 5:
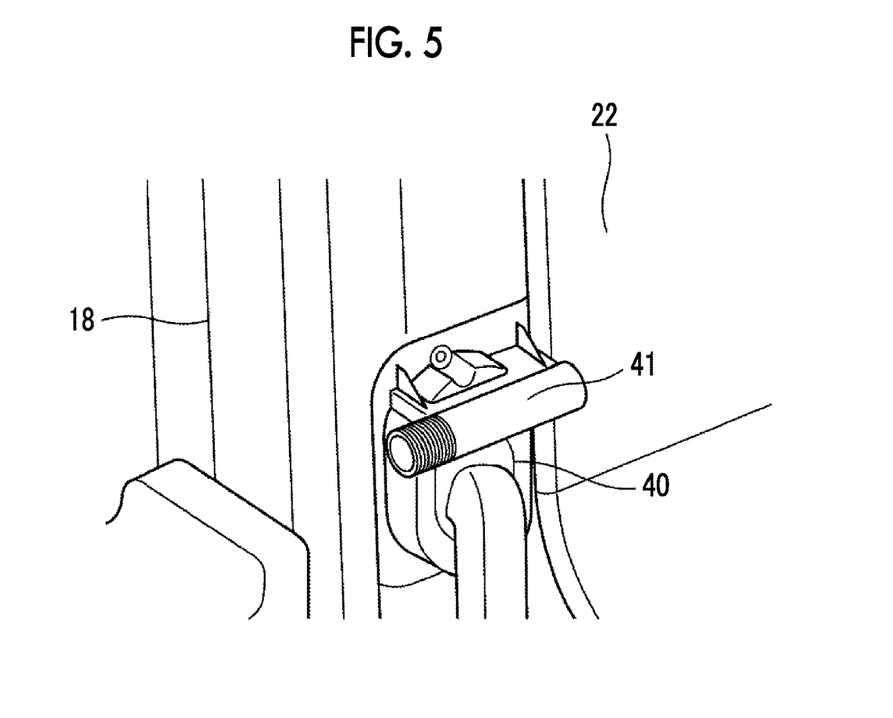
FIG. 5 is a perspective view showing main parts for illustrating attachment of the protection part to a holding part of the mammography apparatus according to the embodiment.
Figure 6:
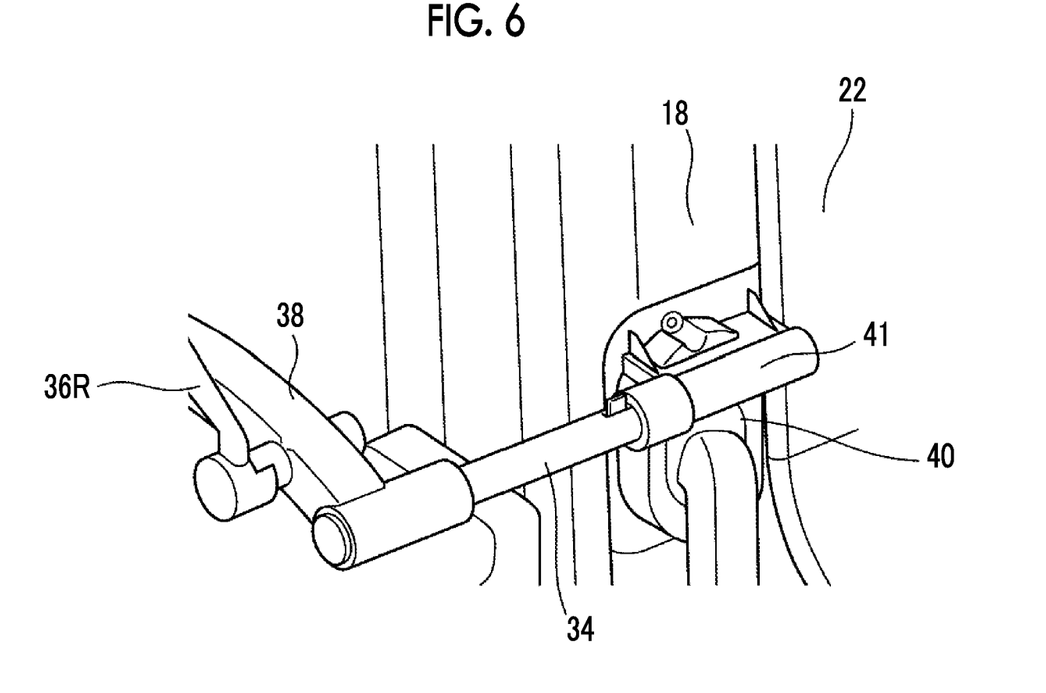
FIG. 6 is a perspective view showing main parts for illustrating attachment of the protection part to a holding part of the mammography apparatus according to the embodiment.

In the mammography apparatus 10 of this embodiment, as shown in FIG. 5, a detachable connection part 40 for detachably attaching the protection part 30 is provided on each side surface of the holding part 18. The insertion part 34B of the attachment part 34 of the protection part 30 is inserted into each of tube parts 41 provided in the detachable connection part 40, as shown in FIG. 6. The insertion part 34B inserted into the tube part 41 is fixed to the detachable connection part 40 so as not to be pulled out of the detachable connection part 40 using a fixing member such as a spring (not shown) provided in the tube part 41.

Next, an operation of the mammography apparatus 10 according to this embodiment will be described with reference to the accompanying drawings. In a case where imaging of mammae of a test subject is performed, a user such as a doctor or a radiation technician positions the mammae of the test subject on the imaging surface 24 of the imaging stand 16 of the mammography apparatus 10, and presses the mammae between the imaging stand 16 and the pressing plate 20 to be fixed using the pressing plate 20. Further, the test subject is fixed with the face of the test subject (head portion) being in contact with the face guard 32, for example.

Figure 7:
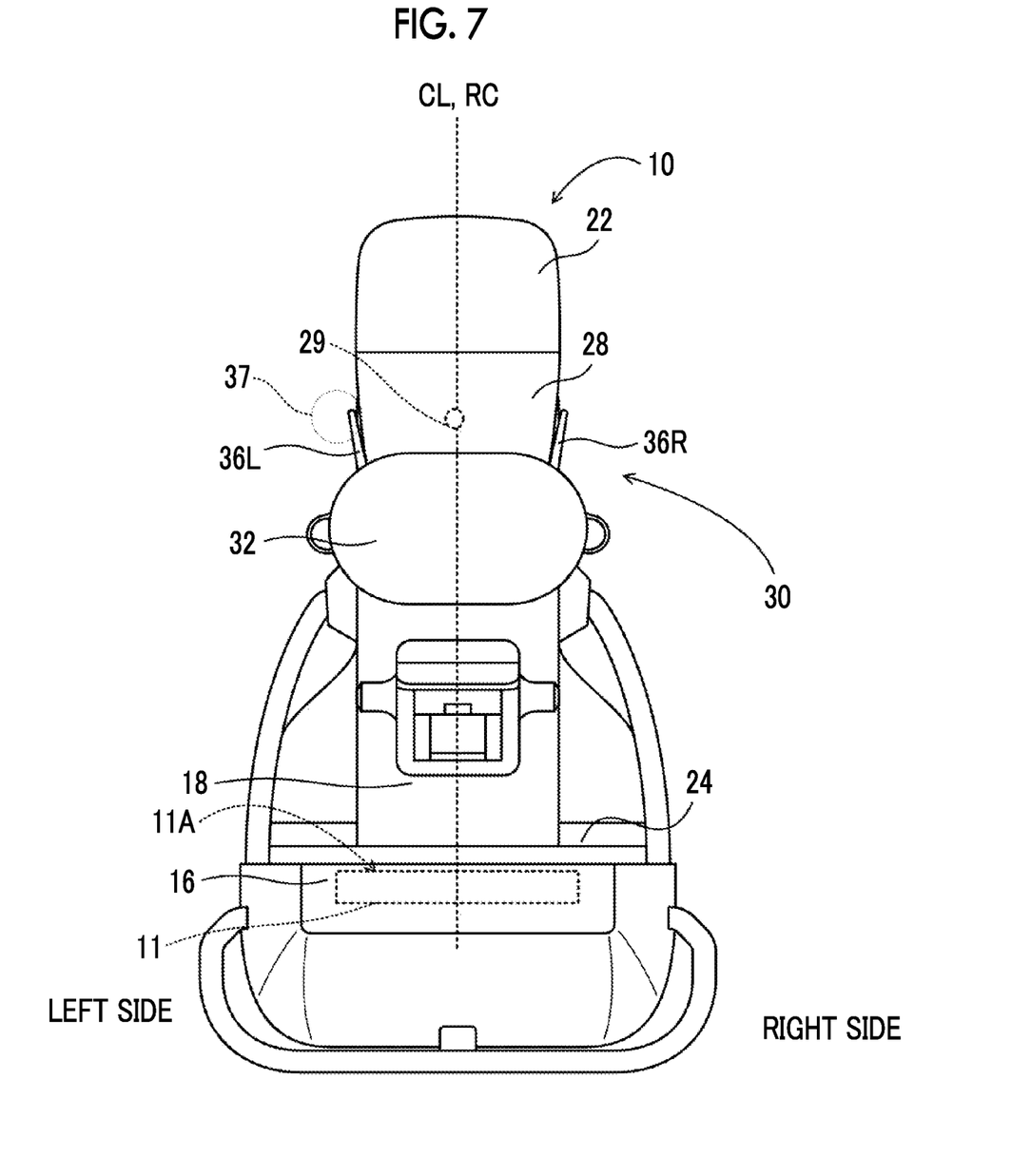
FIG. 7 is a front view showing an example of a configuration of main parts in the case of normal imaging of the mammography apparatus according to the embodiment, when seen from a test subject side.

In a case where the mammography apparatus 10 according to this embodiment performs normal imaging, the radiation source 29 is disposed by the support part 22 at a position where an incidence angle of radiation is 0, and radiation is emitted from the radiation source 29 to perform imaging of the mammae of the test subject. FIG. 7 is a front view showing an example of a configuration of main parts of the mammography apparatus 10 in a case where an incidence angle is 0 (normal imaging) in cranio & caudal (CC) imaging in which radiation is emitted in a cranio-caudal (vertical) direction of the test subject, when seen from a test subject side. In the following description, the normal imaging in the CC imaging will be described.

Here, the "incidence angle" refers to an angle formed by a normal line CL of a detection surface 11A of the radiation detector 11 and a radiation axis RC. Accordingly, in a case where the incidence angle is 0, the normal line CL and the radiation axis RC are equal to each other. Further, here, it is assumed that the detection surface 11A of the radiation detector 11 is a surface that is approximately parallel to the imaging surface 24.

As shown in FIG. 7, in the normal imaging, radiation is emitted from the radiation source 29 in a state where the support part 22 is not rotated. Thus, in the case of the normal imaging, each arm 36 of the protection part 30 is in the initial state as it is. That is, in the normal imaging, since the support part 22 is not rotated, the arm 36 of the protection part 30 is not rotated. In this embodiment, at least a part of the arm 36 is in contact with the support part 22 in the initial state.

Figure 8:
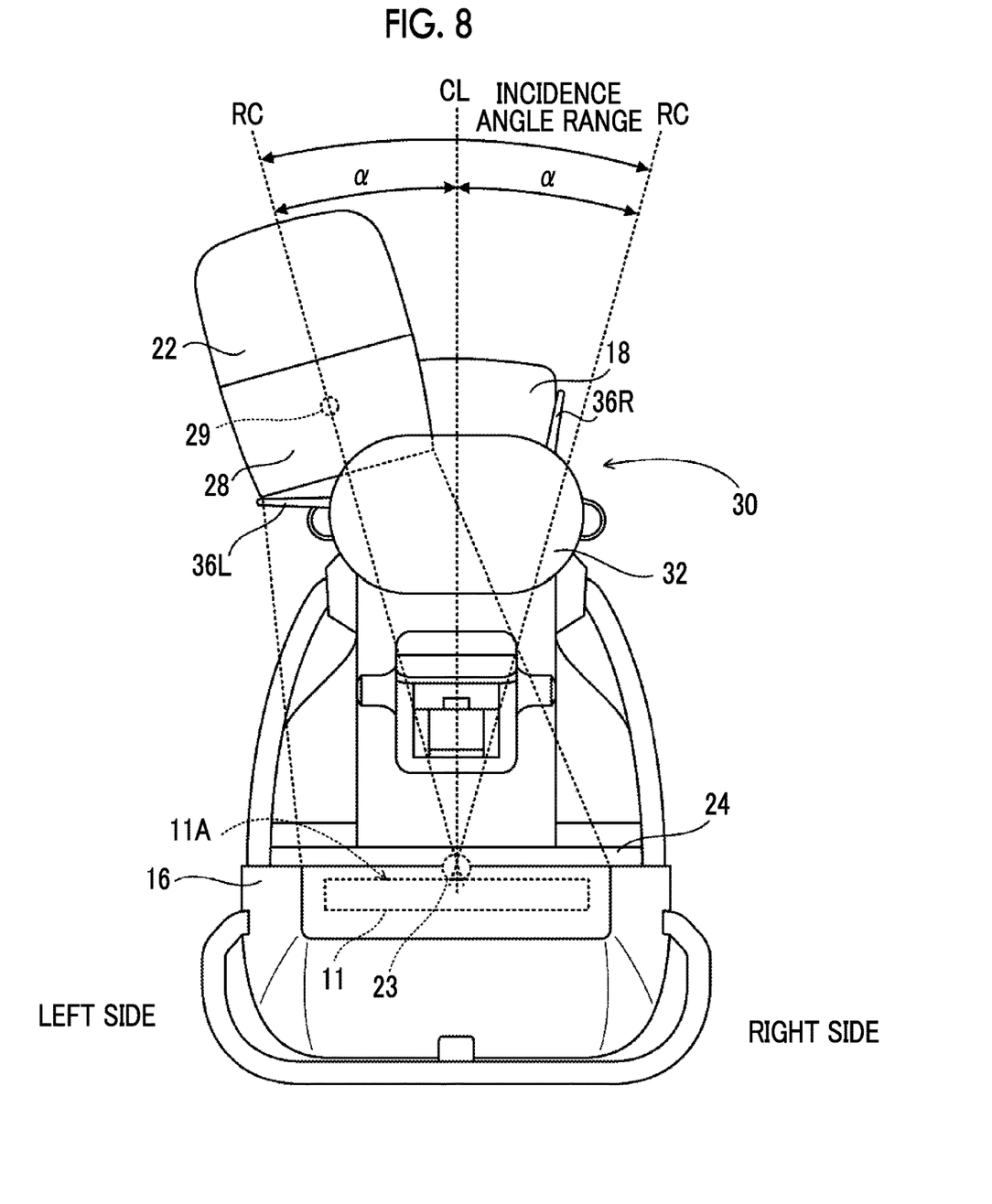
FIG. 8 is a front view showing an example of a configuration of main parts in the case of tomosynthesis imaging of the mammography apparatus according to the embodiment, when seen from a test subject side.

On the other hand, the mammography apparatus 10 according to this embodiment may emit radiation from the radiation source 29 while varying the incidence angle of the radiation in a predetermined range, as shown in FIG. 8, and may perform imaging (so-called tomosynthesis imaging) at each different incidence angle. In this embodiment, the predetermined range where the incidence angle is varied in one-time tomosynthesis imaging is referred to as an "incidence angle range".

In the mammography apparatus 10 according to this embodiment, as shown in FIG. 8, the position of the radiation source 29 is moved so that the incidence angle of the radiation is changed from an angle α at an interval of a predetermined angle θ, and imaging is performed whenever the radiation source 29 is positioned at each of imaging positions of a plurality of places. The incidence angle range of the radiation may be a range of ±7.5°, ±12.5°, ±20°, or the like with respect to the normal line CL, for example.

In the mammography apparatus 10 of this embodiment, in a case where the tomosynthesis imaging is performed, imaging is performed at each imaging position while continuously moving the radiation source 29. As an imaging method in a case where the radiation source 29 is continuously moved, for example, a method for continuously moving the radiation source 29 without stoppage, emitting radiation to mammae from the radiation source 29 in a case where the radiation source 29 reaches each imaging position, and performing imaging using the radiation detector 11 in synchronization with a timing of the emission may be used.

Figure 9:
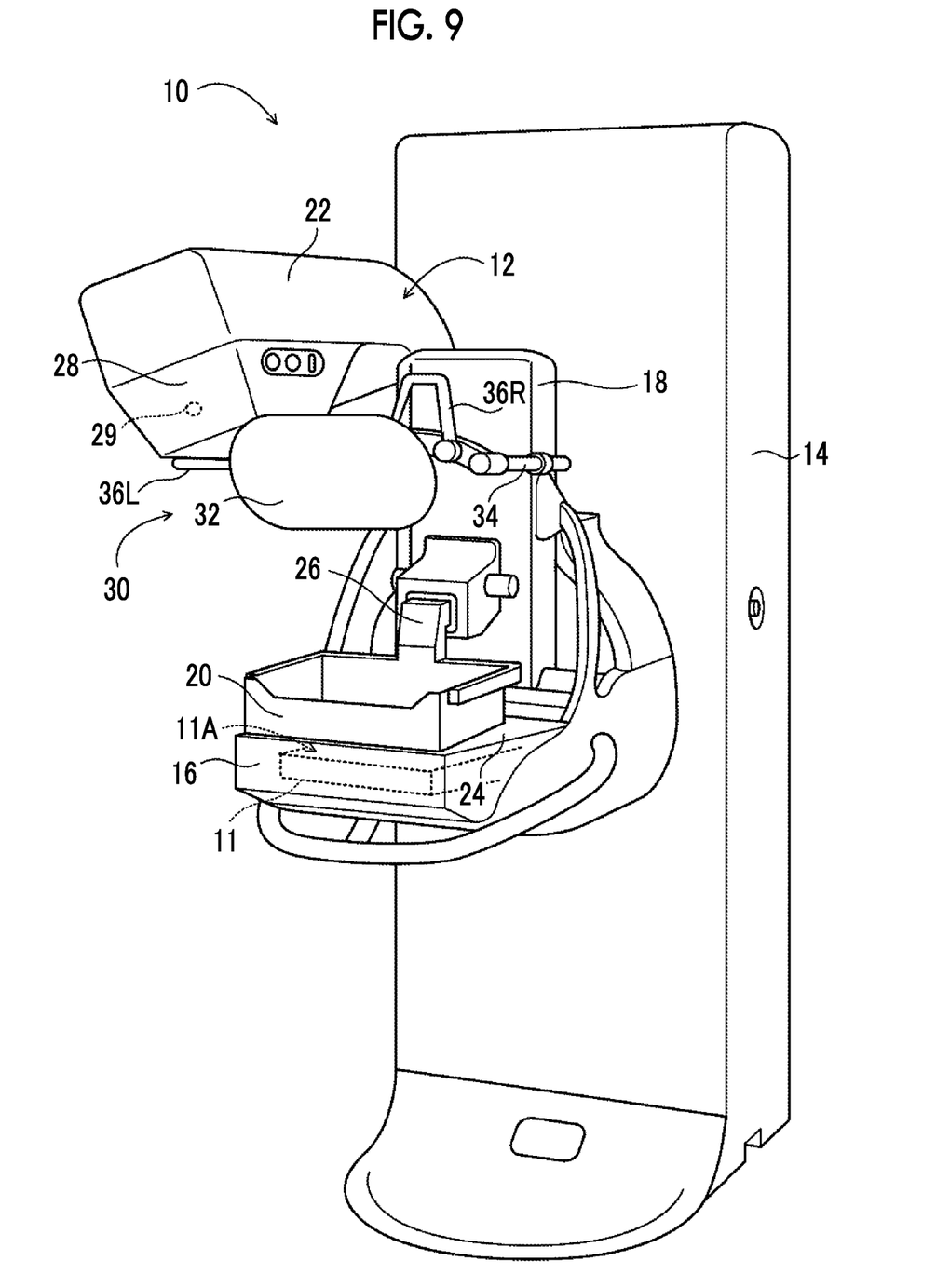
FIG. 9 is a perspective view showing an example of a configuration of main parts in the case of tomosynthesis imaging of the mammography apparatus according to the embodiment.

In the mammography apparatus 10 of this embodiment, as shown in FIGS. 8 and 9, in a case where the tomosynthesis imaging is performed, the radiation source 29 is moved from a left side of the test subject toward a right side thereof. Accordingly, in the mammography apparatus 10, first, the support part 22 is rotated to move the radiation source 29 from the position in the initial state (see FIG. 7) to an imaging start position. In the mammography apparatus 10 of this embodiment, it is assumed that the position of the support part 22 (radiation source 29) in the initial state is the same as the position where the incidence angle of the radiation is 0, that is, the position in the normal imaging.

The arms 36 of the protection part 30 are rotated by being pressed against the radiation emission part 28 of the support part 22 in accordance with the rotation of the support part 22.

Accordingly, in the mammography apparatus 10 of this embodiment, in a case where the support part 22 is rotated in a direction from the initial state toward the left side of the test subject, the arm 36L is rotated, and in a case where the support part 22 is rotated in a direction from the initial state to the left side of the test subject, the arm 36R is rotated. With respect to the rotation direction of the support part 22 in this embodiment, the direction toward the left side of the test subject corresponds to an example of a first direction according to the present disclosure, and the direction toward the right side of the test subject corresponds to an example of a second direction according to the present disclosure.

A state shown in FIGS. 8 and 9 represents a state where the arm 36L is rotated by the support part 22 from the initial state. On the other hand, in the state shown in FIGS. 8 and 9, since the arm 36R is not pressed by the support part 22, the arm 36R is not rotated and maintains the initial state.

In this case, in the mammography apparatus 10 of this embodiment, as shown in FIGS. 8 and 9, the arm 36L is pressed by a side surface of the support part 22, and the arm 36 does not enter into an irradiation field 100 of radiation emitted from the radiation source 29.

In a case where the support part 22 starts rotation to move the radiation source 29, as described above, since a force is applied to the arm 36L in a direction of returning to the initial state, the arm 36L is also rotated in a direction of returning to the initial state in accordance with the rotation of the support part 22.

In a case where the support part 22 is rotated up to a state where the incidence angle of radiation is 0 (see FIG. 7), the arm 36L returns to the initial state and stops the rotation. In a case where the support part 22 is further rotated, the arm 36L instead of the arm 36R starts rotation while being pressed by the radiation emission part 28 of the support part 22 in accordance with the rotation of the support part 22.

Even in a case where the arms 36 are rotated in this way, in the mammography apparatus 10 of this embodiment, since the rotation axes 35 of the arms 36 are arranged along the axis 23 that is the rotation axis of the support part 22, the face guard 32 is not moved.

As described above, the mammography apparatus 10 of this embodiment includes the radiation source 29 that emits radiation to mammae of a test subject, the support part 22 that supports the radiation source 29 to be rotatable around the axis 23 and moves the radiation source 29 to a plurality of imaging positions where incidence angles of the radiation to the mammae are different from each other, the face guard 32 that protects the test subject from radiation emitted from the radiation source 29, and at least one pair of arms 36 that is rotatably connected to the face guard 32 at one end thereof, is rotatably connected to the holding part 18 that maintains a stationary state with respect to the rotation of the radiation source 29 at the other end thereof, includes the bending part 37 between the one end and the other end, and is rotatable around the rotation axis 35 that connects the one end and the other end.

For example, unlike the mammography apparatus 10 of this embodiment, in a case where the face guard 32 is moved in accordance with the rotation of the support part 22, it may be necessary that a large face guard that protects a test subject is provided over a range (incidence angle range) where the support part 22 is rotated. Alternatively, it is necessary that a mechanism that moves the face guard 32 in accordance with the rotation of the support part 22 is provided. Accordingly, in such a case, there is a tendency that the size of the mammography apparatus 10 is increased.

On the other hand, in the mammography apparatus 10 of this embodiment, since the arms 36 of the protection part 30 are configured to be rotatable by the rotation axis 35, even in a case where the support part 22 is rotated, the face guard 32 is not rotated. Accordingly, in the mammography apparatus 10 of this embodiment, in a case where the face guard 32 that protects a test subject in the tomosynthesis imaging in which imaging is performed while moving the radiation source 29 is provided, it is possible to prevent an increase in the size of the mammography apparatus 10.

Further, unlike the mammography apparatus 10 of this embodiment, in a case where the face guard 32 is moved, it is difficult to perform the tomosynthesis imaging in a state where a test subject brings the face (head portion) into contact with the face guard 32.

On the other hand, in the mammography apparatus 10 of this embodiment, since the face guard 32 is not moved, it is possible to perform the tomosynthesis imaging in a state where a test subject brings the face (head portion) into contact with the face guard 32. Accordingly, according to the mammography apparatus 10 of this embodiment, it is possible to stably fix a test subject even in the tomosynthesis imaging, and also, to reduce the burden of the test subject.

Further, even in a case where the face guard 32 is not moved in accordance with the rotation of the support part 22, for example, in a case where the arms 36 of the protection part 30 are not rotated unlike the mammography apparatus 10 of this embodiment, for example, in order to prevent the arms 36 from entering the irradiation field 100 of radiation, the arms 36 become large, which causes an increase in the size of the mammography apparatus 10. In addition, in this case, the arms 36 become obstacles, and thus, it is difficult for a user to position a test subject.

On the other hand, according to the mammography apparatus 10 of this embodiment, since the arms 36 are rotated outside the irradiation field 100 in accordance with the rotation of the support part 22, the arms 36 do not enter the irradiation field 100 during imaging for a radiation image. Accordingly, in a case where the face guard 32 that protects a test subject in the tomosynthesis imaging in which imaging is performed while moving the radiation source 29 is provided in the mammography apparatus 10 of this embodiment, it is possible to prevent an increase in the size of the mammography apparatus 10. Further, according to the mammography apparatus 10 of this embodiment, it is possible to prevent the arms 36 from becoming obstacles, and thus, it is possible for a user to easily position a test subject.

In this embodiment, a configuration in which the arms 36 are rotated by being pressed by the radiation emission part 28 of the support part 22 in accordance with the rotation of the support part 22 has been described, but a method for rotating the arms 36 is not limited thereto. For example, a configuration in which a user rotates the arms 36 in advance from the initial state before the tomosynthesis imaging is started and the user returns the arms 36 to the initial state after the imaging is terminated may be used. Further, for example, a configuration in which a controller (not shown) that controls the rotation of the support part 22 performs a control for rotating the arms 36 on the basis of information indicating the rotation of the support part 22 or performance of the tomosynthesis imaging.

Figure 10:
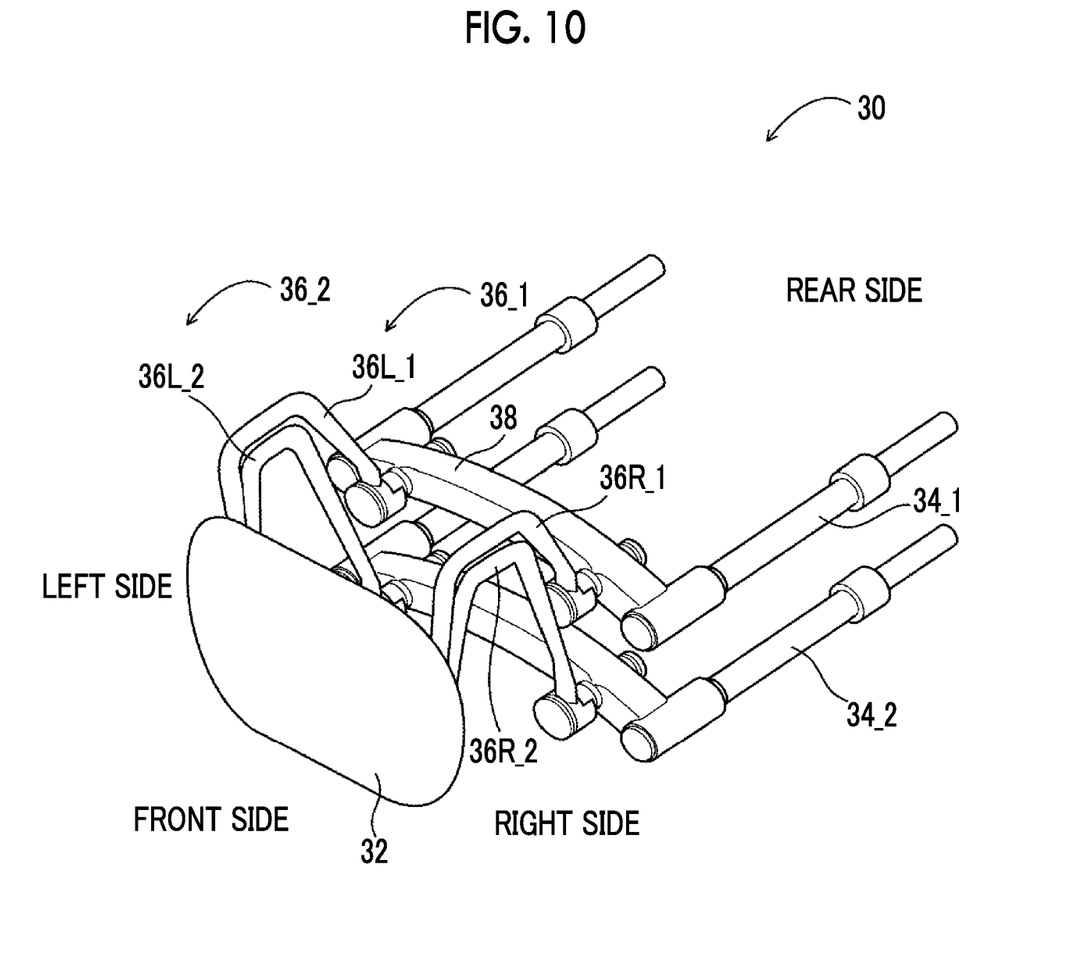
FIG. 10 is a perspective view showing another example of the configuration of the protection part in the mammography apparatus according to the embodiment, when seen from a front side.

Further, in this embodiment, a configuration in which the protection part 30 includes one pair of arms 36, that is, the arm 36L and the arm 36R, has been described, but the invention is not limited thereto, and a configuration in which the protection part 30 includes plural pairs of arms 36 may be used. For example, as shown in FIG. 10, the protection part 30 may include two pairs of arms 36, that is, arms 36_1 and arms 36_2. In the protection part 30 shown in FIG. 10, the arms 36_1 that include an arm 36L_1 and an arm 36R_1 are rotatably connected to the face guard 32, and are attached to the holding part 18 by attachment parts 34_1. Further, the arms 36_2 that include an arm 36L_2 and an arm 36R_2 are provided on a lower side of the arms 36_1, are rotatably connected to the face guard 32, and are attached to the holding part 18 by attachment parts 34_2. In a case where the face guard 32 is large, as shown in FIG. 10, by providing a plurality of pairs of arms 36, it is possible to more stably fix test subject to be in contact with the face guard 32.

Further, in this embodiment, a configuration in which the rotation axis 35 of the protection part 30 extends along (is approximately parallel to) the axis 23 that is the rotation axis of the support part 22 has been described, but a configuration in which the axis 23 is inclined with respect to the rotation axis 35 may be used. For example, a configuration in which the support part 22 is inclined in a front-back direction of a test subject (in a front-back direction of the apparatus) so that the axis 23 is inclined with respect to the imaging surface 24 and the rotation axis 35 is approximately parallel to the imaging surface 24 may be used. In this case, similarly, as the arms 36 are rotated, even in a case where the support part 22 is rotated, the face guard 32 is not rotated.

In addition, in this embodiment, a configuration in which the rotation axis 35 of the protection part 30 is approximately vertical to a surface of the face guard 32 with which the face (head portion) of a test subject is in contact and the holding part 18 has been described, but a configuration in which the rotation axis 35 is inclined with respect to the surface of the face guard 32 with which the face of the test subject is in contact and the holding part 18 may be used. For example, a configuration in which the face guard 32 is in a state where the surface thereof with which the face of the test subject is in contact is provided to be approximately vertical to the imaging surface 24 in a similar way to this embodiment and the attachment part 34 is attached to the holding part 18 in a state where the rotation axis 35 is inclined in a front-back direction of a test subject (in a front-back direction of the apparatus) may be used. In this configuration, similarly, as the arms 36 are rotated, even in a case where the support part 22 is rotated, the face guard 32 is not rotated.

Further, in each of the above-described embodiments, radiation is not particularly limited, and may include X-rays, γ-rays, or the like.

The configurations, operations, and the like of the mammography apparatus 10, the protection part 30, and the like described in each of the above-described embodiments are only examples, and may be modified in accordance with situations in a range without departing from the concept of the invention.

EXPLANATION OF REFERENCES

10: mammography apparatus
11: radiation detector
11A: detection surface
12: imaging part
14: base stand part
16: imaging stand
18: holding part
20: pressing plate
22: support part
23: axis
24: imaging surface
26: support arm
28: radiation emission part
29: radiation source
30: protection part
32: face guard
34, 34_1, 34_2: attachment part
34B: insertion part
34F: support part
35: rotation axis
36, 36_1, 36_2, 36L, 36R, 36L_1, 36L_2, 36R_1, 36R_2: arm
37: bending part
38: connection part
40: detachable connection part
41: tube part
100: irradiation field
CL: normal line
RC: radiation axis
α: angle

What is claimed is:
1. A mammography apparatus comprising:
a radiation source that emits radiation to mammae of a test subject;
a support that is configured to support the radiation source, wherein the radiation source is rotatable around a first rotation axis and movable to a plurality of imaging positions at which incidence angles of the radiation to the mammae are different from each other;
a protection member that protects the test subject from the radiation emitted from the radiation source; and
at least one pair of arms, each of which is rotatably and directly connected to the protection member at one end thereof, is rotatably connected to a stationary imaging stand holder that remains stationary with respect to the rotation of the radiation source at the other end thereof, includes a bent portion between the one end and the other end, and is rotatable around a second rotation axis that connects the one end and the other end.

2. The mammography apparatus according to claim 1, wherein the pair of arms is rotated outside an irradiation field of the radiation.

3. The mammography apparatus according to claim 1, wherein the pair of arms includes an arm that is rotated in a case in which the support is rotated in a first direction from an initial state, and an arm that is rotated in a case in which the support part is rotated in a second direction from the initial state.

4. The mammography apparatus according to claim 3, wherein the arms are rotated in a direction in which the support is rotated.

5. The mammography apparatus according to claim 1, wherein the arms are rotated by being pressed by the support in accordance with the rotation of the support.

6. The mammography apparatus according to claim 1, wherein the stationary part includes connectors to which the arms are detachably connected.

7. The mammography apparatus according to claim 1, wherein each bent portion of the pair of arms protrudes upward in a case in which the support is not rotated.

8. The mammography apparatus according to claim 1, wherein a force is applied to each of the pair of arms in a direction in which the support returns to an initial state from a rotated state.

9. The mammography apparatus according to claim 1, wherein, in a case in which the support is not rotated, each of the pair of arms is in contact with the support.

10. The mammography apparatus according to claim 1, wherein the stationary imaging stand holder holds an imaging stand that includes an imaging surface that is in contact with the mammae of the test subject, and a pressing plate that presses the mammae.

11. The mammography apparatus according to claim 1, wherein a plane, in which each of the arms extends, intersects another plane, in which the protection member extends.

12. The mammography apparatus according to claim 11, wherein the plane, in which each of the arms extends, is substantially perpendicular to the other plane, in which the protection member extends.

* * * * *